Figure 1:
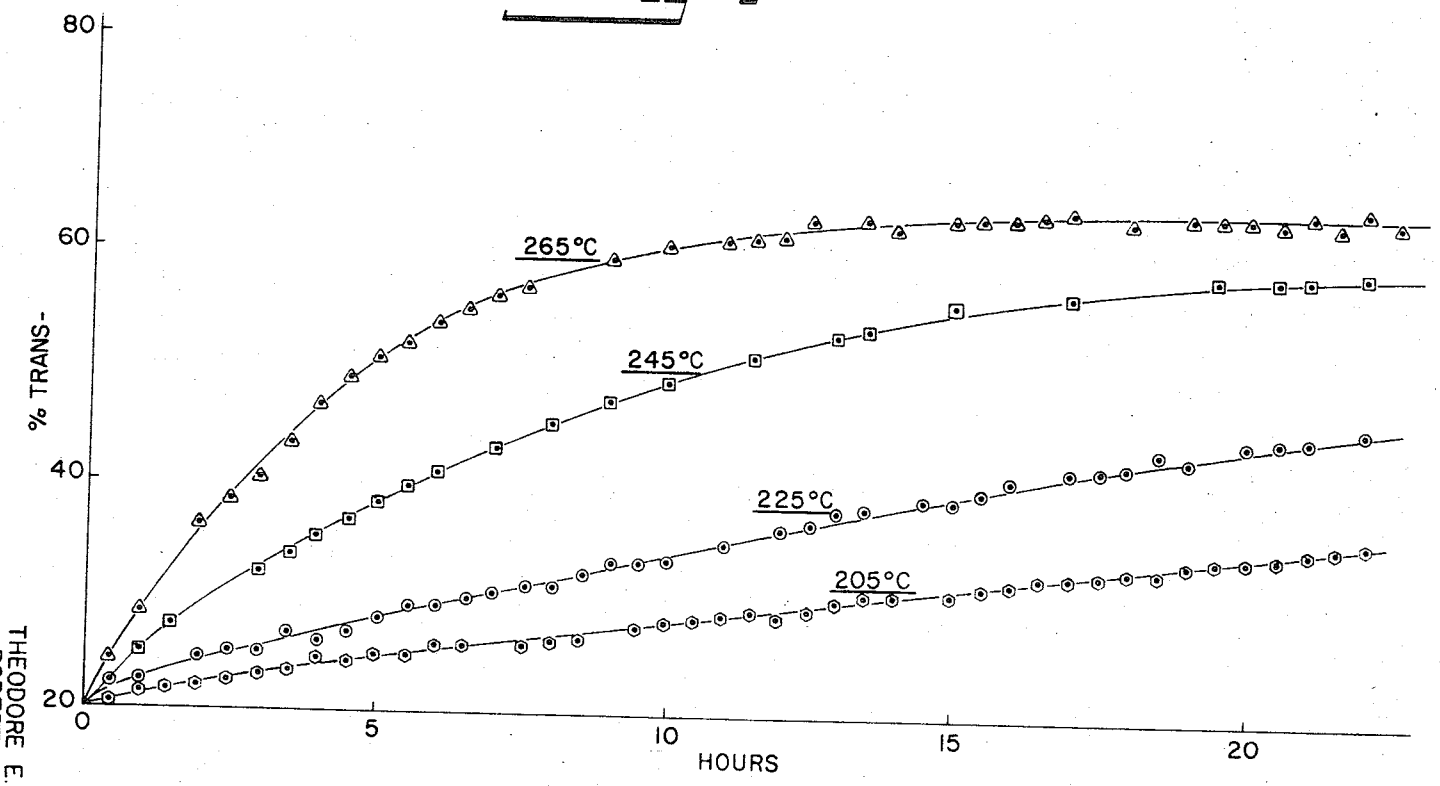

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JUNE 26, 1973

911 O.G. 1138

T911,020

ISOMERIZATION OF CYCLOHEXANE-DICARBOXYLIC ACID ESTERS

Theodore Edward Stanin, 1300 Greenfield Place 37662, and Robert Estes Gee, Jr., 2140 Swannanoa Ave. 37664, both of Kingsport, Tenn.

Continuation of abandoned application Ser. No. 114,432, Feb. 11, 1971. This application Nov. 3, 1972, Ser. No. 303,590

Int. Cl. C07c *69/74*

U.S. Cl. 260—468 K

2 Sheets Drawing. 11 Pages Specification

Organic carboxylic acids have been found to be active catalysts for the isomerization of cis-1,4- and cis-1,3-cyclohexanedicarboxylic acid dialkyl esters into their corresponding trans derivatives. The preferred isomerization catalysts are the dicarboxylic acids and their monoesters, (such as trans-1,4-cyclohexanedicarboxylic acid or its monoester), since these compounds need not be removed from the product preliminary to use of the isomerizate product in polyester manufacture.

ISOMERIZATION OF CYCLOHEXANEDICARBOXYLIC ACID ESTERS

Original Filed Feb. 11, 1971

2 Sheets-Sheet 1

THEODORE E. STANIN
ROBERT E. GEE, JR
INVENTORS

BY

ATTORNEYS

ISOMERIZATION OF CYCLOHEXANEDICARBOXYLIC ACID ESTERS
Original Filed Feb. 11, 1971 2 Sheets-Sheet 2
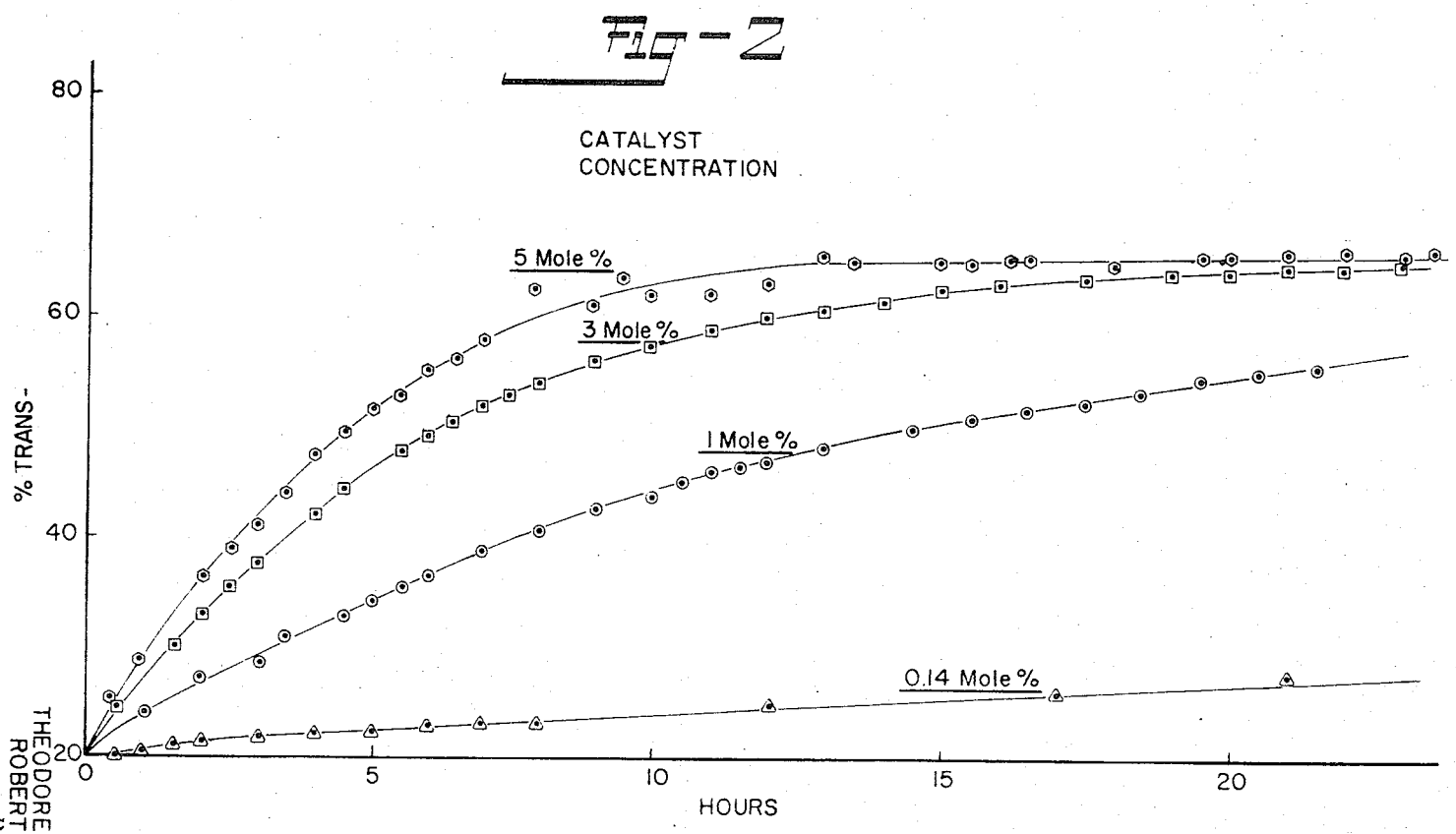
THEODORE E. STANIN
ROBERT E. GEE, JR.
INVENTORS
BY
ATTORNEYS